(12) United States Patent
Schlote-Holubek et al.

(10) Patent No.: US 7,471,034 B2
(45) Date of Patent: Dec. 30, 2008

(54) ULTRASOUND TRANSDUCER AND METHOD OF PRODUCING THE SAME

(75) Inventors: Klaus Schlote-Holubek, Karlsruhe (DE); Georg Göbel, Karlsruhe (DE); Rainer Stotzka, Karlsruhe (DE)

(73) Assignee: Forschungszentrum Karlsruhe GmbH, Karlsruhe (DE)

( * ) Notice: Subject to any disclaimer, the term of this patent is extended or adjusted under 35 U.S.C. 154(b) by 279 days.

(21) Appl. No.: 11/453,525

(22) Filed: Jun. 15, 2006

(65) Prior Publication Data

US 2006/0230605 A1 Oct. 19, 2006

Related U.S. Application Data

(63) Continuation-in-part of application No. PCT/EP2005/004389, filed on Apr. 23, 2005.

(30) Foreign Application Priority Data

May 8, 2004 (DE) .......... 10 2004 022 838

(51) Int. Cl.
  *H01L 41/08* (2006.01)
(52) U.S. Cl. .......... 310/348; 310/322; 310/326; 310/334; 310/367
(58) Field of Classification Search .......... 310/322, 310/326, 327, 334, 340, 345, 348, 367, 368
See application file for complete search history.

(56) References Cited

U.S. PATENT DOCUMENTS

| 2,716,708 | A | * | 8/1955 | Bradfield | 310/317 |
| 4,184,094 | A | * | 1/1980 | Kopel | 310/335 |
| 4,500,807 | A | * | 2/1985 | Yuhara et al. | 310/313 B |
| 4,672,591 | A | * | 6/1987 | Breimesser et al. | 367/152 |
| 5,349,568 | A | * | 9/1994 | Kupperman et al. | 367/125 |
| 6,538,361 | B2 | * | 3/2003 | Yoshida | 310/320 |
| 2002/0003385 | A1 | * | 1/2002 | Jones | 310/334 |
| 2002/0044171 | A1 | * | 4/2002 | Hirahara et al. | 347/46 |

FOREIGN PATENT DOCUMENTS

| EP | 1 145 772 | | 1/2001 | |
| JP | 55-100718 | * | 7/1980 | 310/340 |
| WO | WO 02/40184 | | 5/2002 | |
| WO | WO 03/047770 | | 6/2003 | |

* cited by examiner

*Primary Examiner*—Thomas M Dougherty
(74) *Attorney, Agent, or Firm*—Klaus J. Bach (57) ABSTRACT

In an ultrasound transducer arrangement comprising at least one piezoelectric body with a lower and an upper electrode and a coupling layer including a wafer on which the ultrasound transducers are disposed and are connected to the lower electrode, a conductor structure of uniform height is disposed on the wafer and is in contact with the lower electrode and any space between the piezoelectric body and the wafer is completely filled with a cement material.

9 Claims, 5 Drawing Sheets

ULTRASOUND TRANSDUCER AND METHOD OF PRODUCING THE SAME

This is a Continuation-In-Part Application of International Application PCT/EP2005/004389 filed Apr. 23, 2005 and claiming the priority of German Application 10 2004022838.8 filed May 8, 2004.

BACKGROUND OF THE INVENTION

The present invention relates to an ultrasound transducer, comprising at least one piezoelectric body with at least one lower and one upper electrode and a coupling layer with on a wafer surface on which the ultrasound transducer is disposed and connected to the lower electrode and to a method of manufacturing such an ultrasound transducer.

Like in many areas of electronic devices and sensors, the components for the apparatus and the systems continue to become smaller and more powerful also for ultrasound systems. An important part of such systems are ultrasound sensors, which, in most cases, are designed specifically for a particular measuring problem. Costs and quality of components are both very important in the development of ultrasound systems. It is essential that in multi-transducer systems the ultrasound transducers have all the same acoustical and electrical properties.

Examples for the high development state of ultrasound testing equipment are ultrasound transducer arrays or also group transducers. A transducer array comprises a number of individual transducer elements, preferably columns or strips which, for physical reasons, must be very small and arranged tightly adjacent one another in order to deflect the acoustic signal into the desired direction for example by a phase-modified control of the individual transducer elements or groups. The size of such individual transducer elements and their distances from one another are below 0.5 mm at a frequency of the transducer elements of 5 MHz.

With such arrangements, it is possible to swipe the medium to be examined without changing the position of the ultrasound transducer head. The transducers may then be disposed in a linear array or in a matrix structure. This type of ultrasound transducers are often used in material testing and for medical applications.

[2] discloses, for example in connection with the use of ultrasound computer tomography (USCT) for early breast cancer detection, a special arrangement of the newest generation of ultrasound transducers of the type referred to above. For such a system, a large number of ultrasound transducers of small size (for example, 1×1 mm) is required, which are effective, approximately, as point-like radiation emitters. They are arranged around an examination volume as a matrix structure in the form of a cylinder or in the form of a semi-sphere whereby spatial information (3D) can be obtained from the volume to be examined without mechanical movement of any of the ultrasound transducers. This measuring arrangement in connection with a parallel signal processing unit is suitable for a complete tomographic examination of a body part of a patient with measuring times of less than 0.05 s, so that a chronology if individual images is really becoming negligibly important. The high number (several thousands) of ultrasound transducers of small size corresponds in principle to a cylinder shaped or sphere-shaped ultrasound transducer array with the individual ultrasound transducers forming the transducer elements.

The acoustic properties depend physically directly on the geometric data of ultrasound transducers, particularly the coupling layer and transducer element (usually a piezo-electric body). Manufacturing accuracies and tolerance ranges in the production of ultrasound transducers affect the accuracy and tolerance width of acoustic properties of an ultrasound transducer manufacturing series. Even though small deviations of the acoustic properties can be compensated for electronically within a certain bandwidth or can be limited by a subsequent quality control, it is necessary already for economical reasons that the ultrasound transducers have predetermined acoustic and electric properties within a narrow tolerance widths.

The coupling- or adaptation layer is provided for a low-loss coupling of a transducer element to a medium. It compensates for different acoustic impedances of a transducer and of water, wherein the thickness of this layer is ideally ¼ of the wavelength of the thickness resonance frequency of the piezo electric body (transducer). Such layers are generally produced from corresponding casting materials which are applied during manufacture to the transducer element which is already contacted and electrically connected. This is followed generally by an adaptation of the coupling layer thickness to the frequency (wavelength) of the transducer element by means of mechanical and therefore expensive follow-up working or fine-cutting of the coupling layer. In accordance therewith, the manufacture of most ultrasound transducers follows a strategy from the inside to the outside, that is, it starts with the transmitter element.

[1] discloses, based on a simple manufacturing capability, an ultrasound transducer and a method of manufacturing such a transducer. In the radiation direction, a piezo-electric body (transducer element) includes a contact area on which a coupling layer is disposed. The contacts on the opposite electrode surface of the body, on the other hand, is provided by a conductor foil which is cemented or pressed onto the electrode surface. The conductor foil is held pressed in contact with the electrode surface for example mechanically by an attenuation body. With the arrangement of the conductor layers on the conductor foil, individual areas of the body or of the transducer are selectively controllable. The electrode at the radiation emitting side itself does not include any conductor structure.

Such an ultrasound transducer still requires a coupling layer which is mounted as a separate component onto the electrode at the radiation emitting side. Furthermore, the connections to the two electrodes are established by individual wire connections which requires a comparatively high manufacturing expenditures.

In [3] an ultrasound transducer system is described wherein several piezo-ceramic bodies, each with an electrode surface are cemented over an area directly onto a conductor plate. The electrodes are connected to sender and receiver electronics on adjacent conductor plates via bonded wires.

Based on this state of the art, it is the object of the present invention to provide an ultrasound transducers which generally facilitates the manufacture thereof, that is, specifically, which provides for an improved accuracy and quality of the coupling layer with smaller tolerance ranges.

SUMMARY OF THE INVENTION

In an ultrasound transducer arrangement comprising at least one piezoelectric body with a lower and an upper electrode surfaces and a coupling layer including a wafer on which the ultrasound transducers are disposed and are connected to the lower electrode, a conductor structure of uniform height is disposed on the wafer and is in contact with the lower electrode and any space between the piezoelectric body and the wafer is completely filled with a cement material.

The piezo electric body is accurately aligned in parallel with one of the two parallel planar electrode surfaces and supported in spaced relationship therefrom by spacers and is reproduceably positioned and fixed on a wafer so as to be in contact therewith. To this end, on the wafer, a conductor structure is disposed which has been etched out of a wafer coating or formed by a thick film technique (for example, by screen printing). The conductor structure serves on one hand to provide the electrical contact with the electrode surface and, on the other hand, with its accurate constant conductor height, to form as spacer between the circuit board and the piezoelectric body over the whole electrode area. For fixing the piezoelectric body on the wafer solder or cement materials are suitable which, upon compression of the piezoelectric body and the wafer, can flow locally into cavities present next to the conductor structure between the wafer and the ultrasound transducer and completely fill those cavities. The piezoelectric body is attached by being pressed onto the conductors wherein the cement or the solder is squeezed out providing for direct contact between the conductor structure and the electrode surface at least at one point. The conductor structure in this way serves at the same time as electrical connection for the emitter-side electrode surface.

The thickness of the coupling layer is ideally $\lambda/4$, wherein coupling layer includes the wafer.

Preferably, the conductor structure extends only below areas of the piezoelectric body which are acoustically inactive or only comparatively slightly active, for example, to the immediate edge areas of the piezoelectric body or the areas in which the piezo electric body is not utilized for the generation or the reception of an ultrasound impulse. "Slightly active"in this connection means that, although in these areas, the ultrasound measuring characteristics of the ultrasound transducer are measurable, it does not detrimentally affect or influence the ultrasound examination. Preferably, the piezoelectric body is not controlled in those areas by the sender or receiver electronics so that these areas can be excluded from the area covered by the upper electrode. The total area of these sections corresponds maximally to 10% of the coverage of the piezoelectric body. Preferably, for avoiding ripple effects, the conductor structures are so formed that a statistically determined support for the lower electrode of the piezoelectric body is provided for example, by way of three support points. Small support points cause, upon pressing the piezoelectric body onto the support, a high area pressure level, that is, tension peaks but advantageously also provide for a high contacting reliability of the electrode by way of the support points.

The quality of the contacting can be tested for example by measuring the ohmic resistance between the two conductors which serve as spacers and which are bridged by the lower electrode.

The required property profile of the plate material is determined particularly by the need for a good sound transmission from the piezoelectric body to a coupling medium into which the ultrasound impulse is fed. Furthermore, the plate material must be inert with respect to the coupling medium, which preferably comprises aqueous solutions or an ultrasound coupling gel as used in medical applications, and it must not absorb the coupling medium or be attached thereto. A material characteristic which is most important for the distribution of the sound waves in a material is the specific acoustic impedance 2 which is defined as the product of the sound speed c and the density p of a material. A fully loss-free sound transmission at an interface area is achieved if the media at both sides of the interface have the same acoustic impedance. With increasing impedance difference, the part reflected at the interface area increases whereby the transmission of an ultrasound signal is detrimentally affected. The difference between the acoustic impedances of two materials or media is therefore a measure for the transmission losses in a transmission of the sound waves from one to another material or medium.

As wafers, commercially available wafers for microwave or high frequency applications may be used which consist of a homogeneous plastic-ceramic compound materials (that is, without fiber inclusions) and which fulfill not only the material requirements for a coupling layer as mentioned above, but which are available advantageously as industrial products of homogeneous and constant material quality and which are reproduceable with the exact geometries and are reasonably priced. The wafers have the important advantage that they are commercially available in various thicknesses and have the required mechanical and chemical properties.

The conductor height determines the distance between the wafer and the lower electrode and, consequently, the cement or solder thickness. Depending on the thickness of this intermediate layer—the thickness is generally between 20 and 7 μm (that is less than $\lambda/4$ at 10 MHz in the wafer)—it is, similar to the metallic electrodes of the piezo-ceramic body (converter), negligible or, if it exceeds a certain thickness, it must be taken into consideration in the calculation of the coupling layer.

In accordance with the invention, the material properties such as the acoustic impedance of the materials used, particularly those of the wafer and the cement must be adapted by suitable measures such as the admixing of substances or powders. Because of the high acoustic impedance values of solders this is not possible in this case. Solders are therefore used preferably only with small conductor heights.

As piezoelectric bodies monolithic unstructured bodies are suitable and also transducers which comprise a multitude of individual transducer elements so as to form a converter array. Particularly in connection with the last mentioned structure, the invention provides for much improved manufacturing capabilities since a first unstructured piezo-electric body is connected to the wafer and is then structured. Using a suitable method such as sawing or ultrasound cutting, the body can be cut into the individual converter elements. The wafer advantageously provides for a suitable mounting arrangement for the manufacturing steps and stabilizes during the segmenting the individual transducer elements on the wafer.

Following the segmenting or structuring, the hollow spaces formed thereby in the area of the body or the transducer element can be filled with suitable materials such as plastic, wherein, in connection with a particular embodiment, these materials may be cementing materials for the cementing of components disposed on the plate such as attenuation bodies.

In this way, also the damping body referred to in the description of the state of the art on the upper, second electrode surface may be replaced by a wafer with a conductor structure of predetermined height.

Alternatively, the cavities mentioned above may remain empty in the area of the body or of the transducer, particularly if the attenuation of the ultrasound transducer provided by the materials is not desired. In this connection, an attenuation body may be attached to the segmented transducer or the structured body as described earlier wherein the individual transducer elements are fixed to both electrode surfaces.

Below the invention will be described on the basis of particular embodiments with reference to the accompanying drawings.

DESCRIPTION OF PREFERRED EMBODIMENTS

Figure 1:
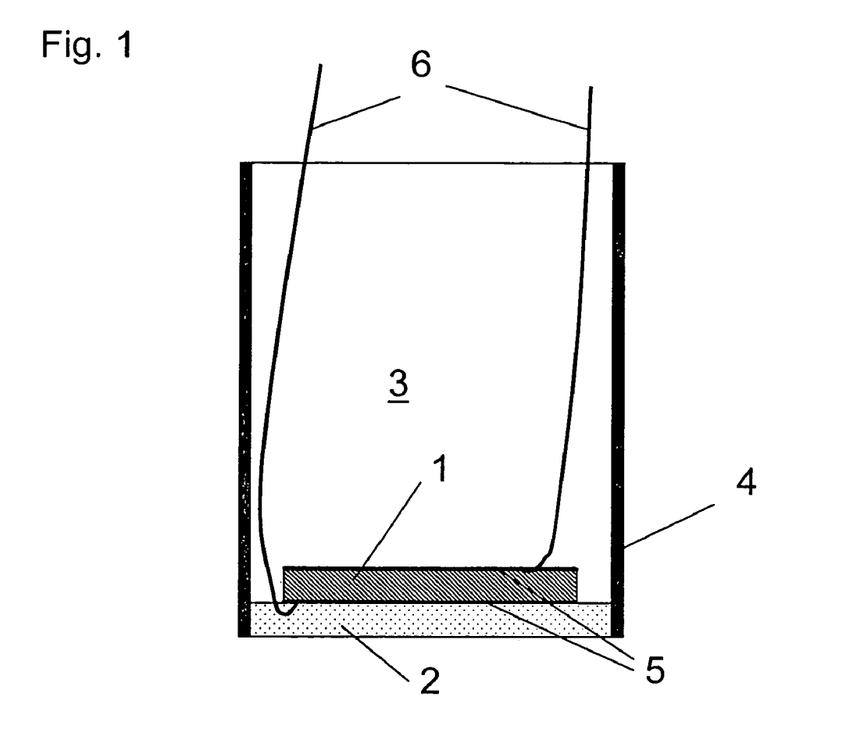
FIG. 1 shows the general arrangement of an ultrasound transducer with components according to the state of the art.

FIG. 1 shows the basic components of an ultrasound transducer of conventional design which includes a piezoelectric body, the transducer 1, which is firmly connected to the coupling layer 2. The coupling layer 2 has a thickness which is ideally ¼ of the wavelength λ and forms the end wall of a housing 4. Within the housing 4, an attenuation body 3 is disposed which, in the present case, is in the form of a casting material. The two electrodes 5 of the transducer 1 are connected to a control and measuring unit, which is not shown, via electrical cable connectors 6. As mentioned initially, the thickness of the coupling layer is obtained by an expensive mechanical finishing operation.

In order to avoid these problems, an HF plate of the type referred to earlier is used as an adaptation layer and holder for the further working. Onto this plate then a piezoelectric transducer is cemented. The wafer used in connection with the exemplary embodiment is suitable for ultrasound transducer systems up to a frequency of about 10 Mhz. It has an acoustic impedance of about 6 to 8 MRayl which is exactly between that of the usual PZT materials of about 20 to 35 MRayl and of water or aqueous solutions of about 1.5 MRayl. The wafers are commercially available in thicknesses of 0.1 to 1.5 mm. based on a coupling layer thickness of the mentioned λ/4, the known commercial plates are suitable for the manufacture of ultrasound transducers with test frequencies in the range of interest for material examination and the medical applications.

FIGS. 2 to 9 show embodiments of the invention in various views.

Figure 2:
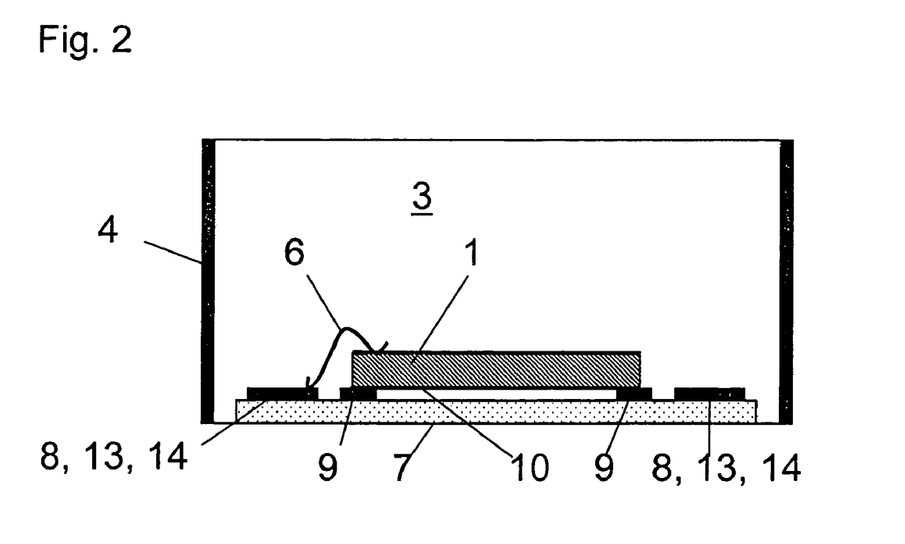
FIG. 2 shows an embodiment of an ultrasound transducer with a monolithic piezoelectric body.
Figure 3:
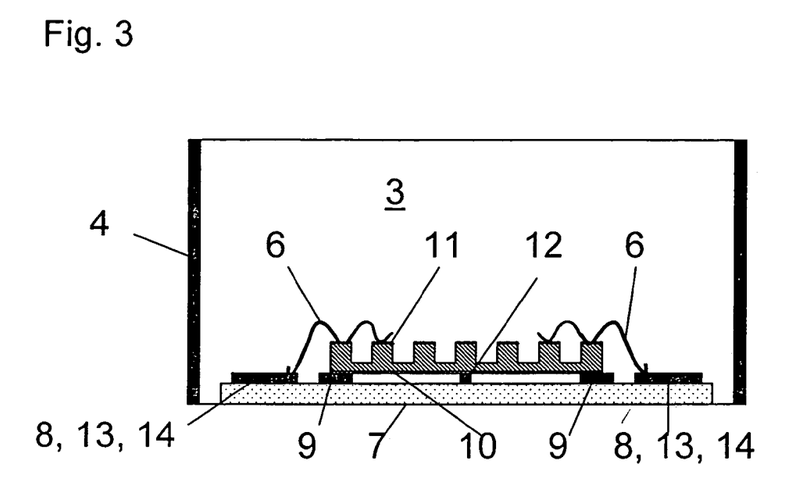
FIG. 3 shows an embodiment of an ultrasound transducer which comprises a plurality of transducer elements.
Figure 4:
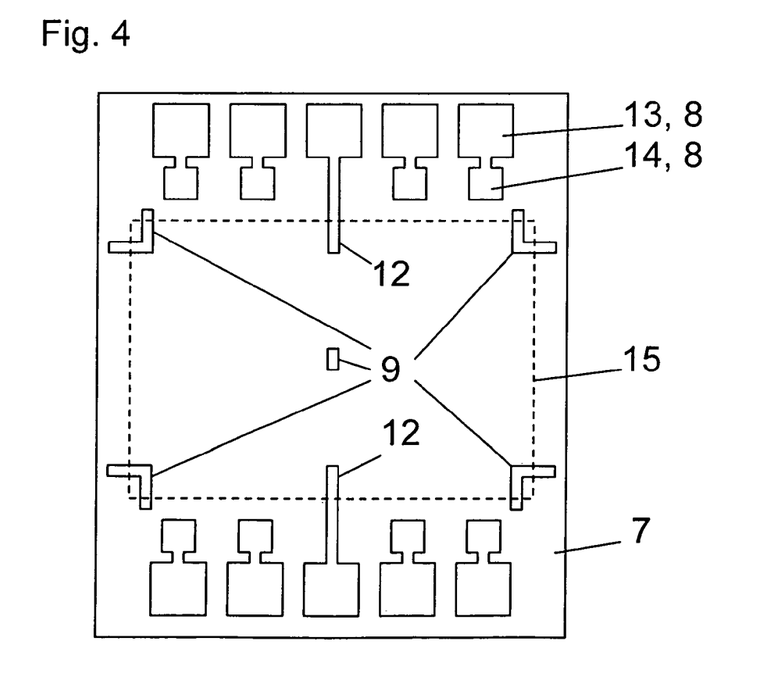
FIG. 4 is a top view of a wafer with a particular exemplary shape.

FIGS. 2 and 3 shows each a side sectional view of an ultrasound transducer, comprising a wafer which includes a conductor structure and a piezo electric body 1 (FIG. 2) or a transducer array 4 (FIG. 3) disposed thereon. FIG. 4 shows in a top view the design of this conductor structure on the plate 7. The conductor structure on the plate comprises outside the cover area 15 of the body 1 or transducer array 11 several contact pads 8 and, within the cover area 15, several spacers 9 without any electrical function and also two ground contacts 12 as electrical contacts for the lower electrode of the transducer or transducer array. The ultrasound transducer is disposed in a housing 4 and is cast therein into the attenuation body 3.

The piezoelectric body or transducer includes two electrodes (upper and lower electrode) which are arranged in parallel spaced planes and have electrode surfaces which are metal coated in the way mentioned earlier. In the embodiment shown in FIG. 2 the piezoelectric body has a cuboid shape. Such a piezoelectric body vibrates with an electrical excitation in three basic frequencies which are determined by the dimensions of the cuboid. To avoid interference of frequencies this effect must be taken into consideration when dimensioning the piezoelectric body.

A transducer as shown in FIG. 3, on the other hand, comprises a larger number of small columns or strips, which are cut out of a piezo-electric body by wire cutting and which are cast by a casting material into a plate or a disc. In the exemplary embodiment, a maximum thickness of the columns was selected which is noticeably smaller than half the wavelength λ/2 in the piezoelectric material of the transducer. Such a transducer has essentially only one oscillation mode that is the thickness vibration. The comparably high radial resonance frequencies can be suppressed effectively by attenuation.

The conductors are etched out of a copper layer applied to an unfinished plate by means of the common etching techniques using photo lacquer and a mask. The conductor height accordingly corresponds to the thickness of the original copper layer whereby a uniform height of the whole conductor structure is ensured with the high manufacturing accuracy of the small tolerance widths of 10% of the copper layer applied to the wafer. Between the piezoelectric body 1 or, respectively, the transducer array 11 and the wafer 7 in the cover area 15, there is a cementing space 10 of the accurately maintainable thickness corresponding to the conductor structure height as shown in FIG. 3. The contact pads 8 which have an electrical connection (conductors) to the ground contacts 12, provide for contact with the lower electrode whereas other contact pads which do not have the electrical connection mentioned are available for bonded (for example, via ultrasound bonding, or spot welding) wire connections to the upper electrodes (see FIGS. 2 and 3).

Figure 5:
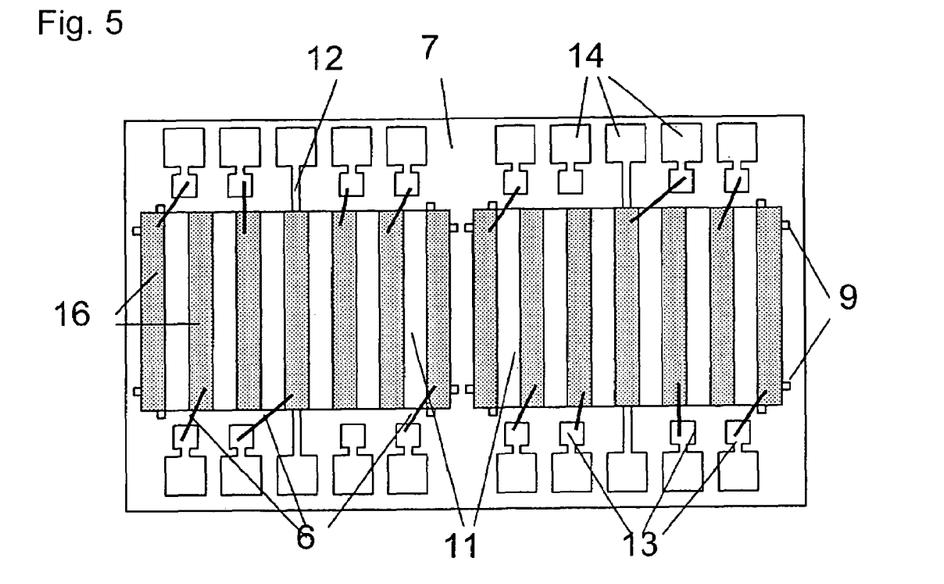
FIGS. 5 and 6 show two more exemplary embodiments of a wafer with transducers disposed thereon.

In this case, the contact pads 8 have a smaller bonding area and a larger solder area electrically connected thereto (see also FIG. 5).

FIG. 4 shows the position of the spacers 9 below the covered area 15. Six of these spacers are disposed in the edge area another spacer is disposed in the center. A central spacer 9 is provided for additional support and is mainly then required when the piezoelectric body, after being put in place and cemented, is worked mechanically, for example, by a wire saw so as to form a transducer array according to FIG. 3 or the ratio of the lateral extension to the thickness of the piezoelectric body exceeds a certain valve. However, it is to be so arranged that the ultrasound signal conducted through the coupling layer is not or very little affected. In the present case, the central spacer is arranged in the center of the sound field that is an ultrasound signal is affected without any preferential direction.

Figure 6:
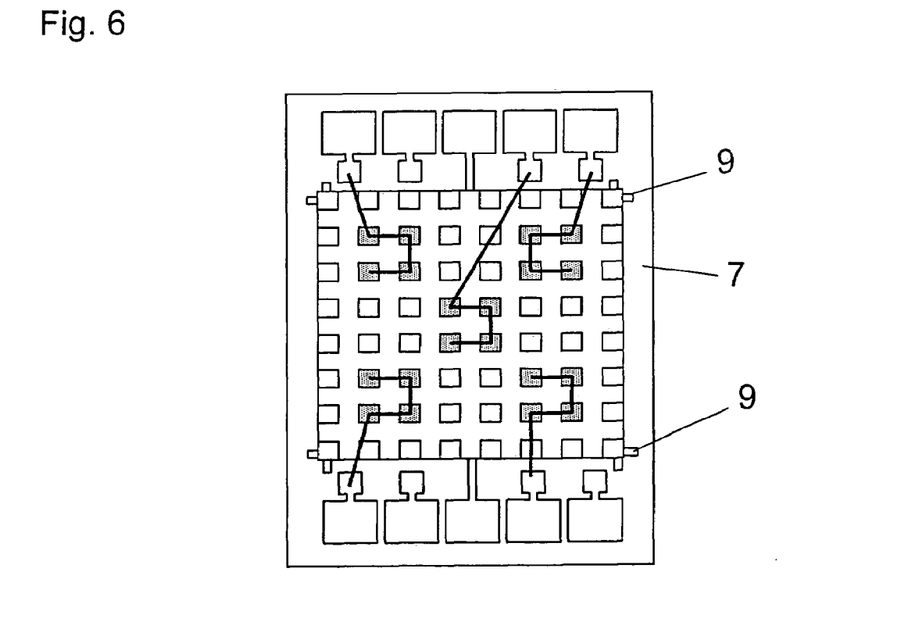
Figure 7:
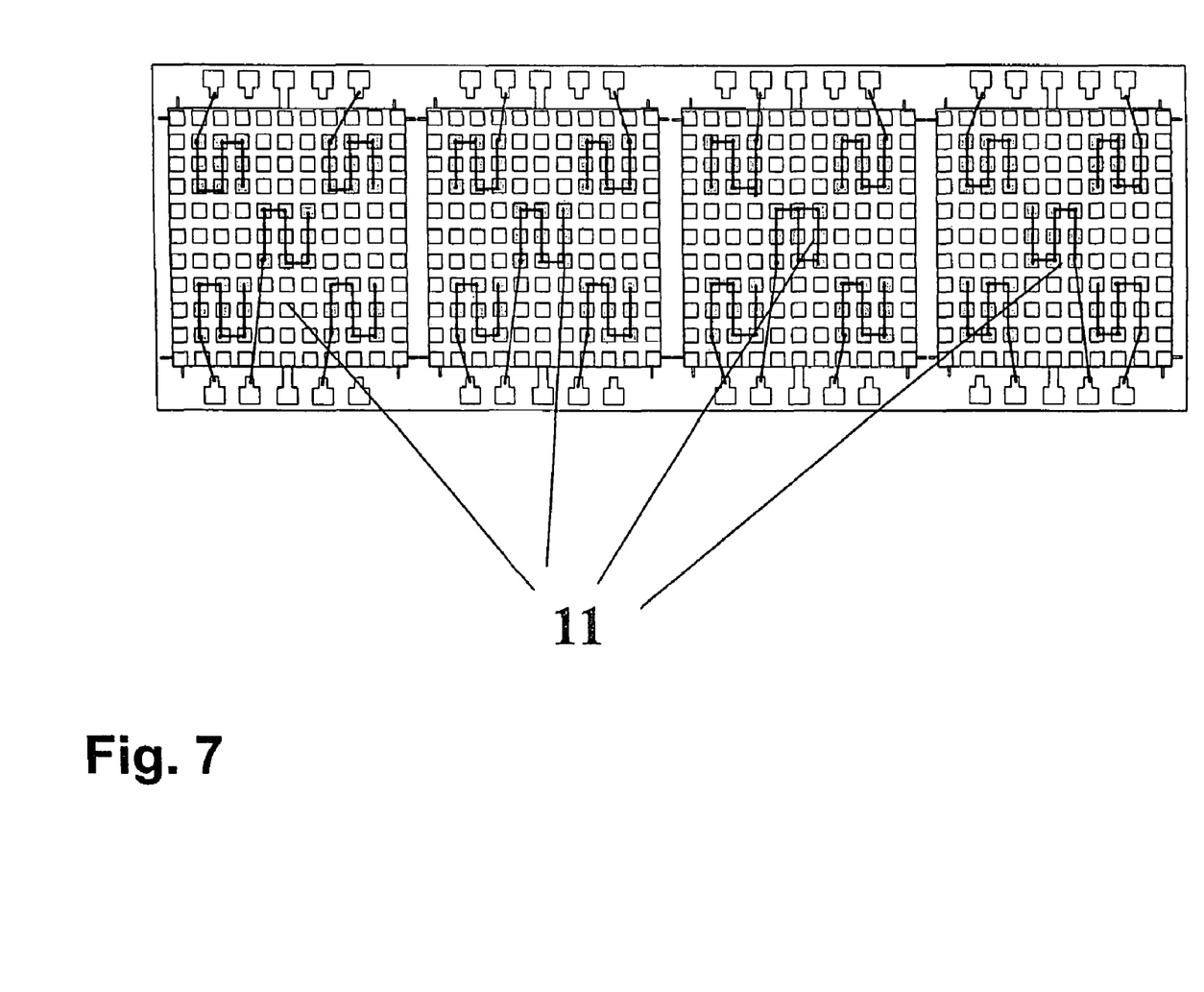
FIGS. 7 and 8 show exemplary embodiments of the wafer with transducers mounted thereon for medical applications.
Figure 8:
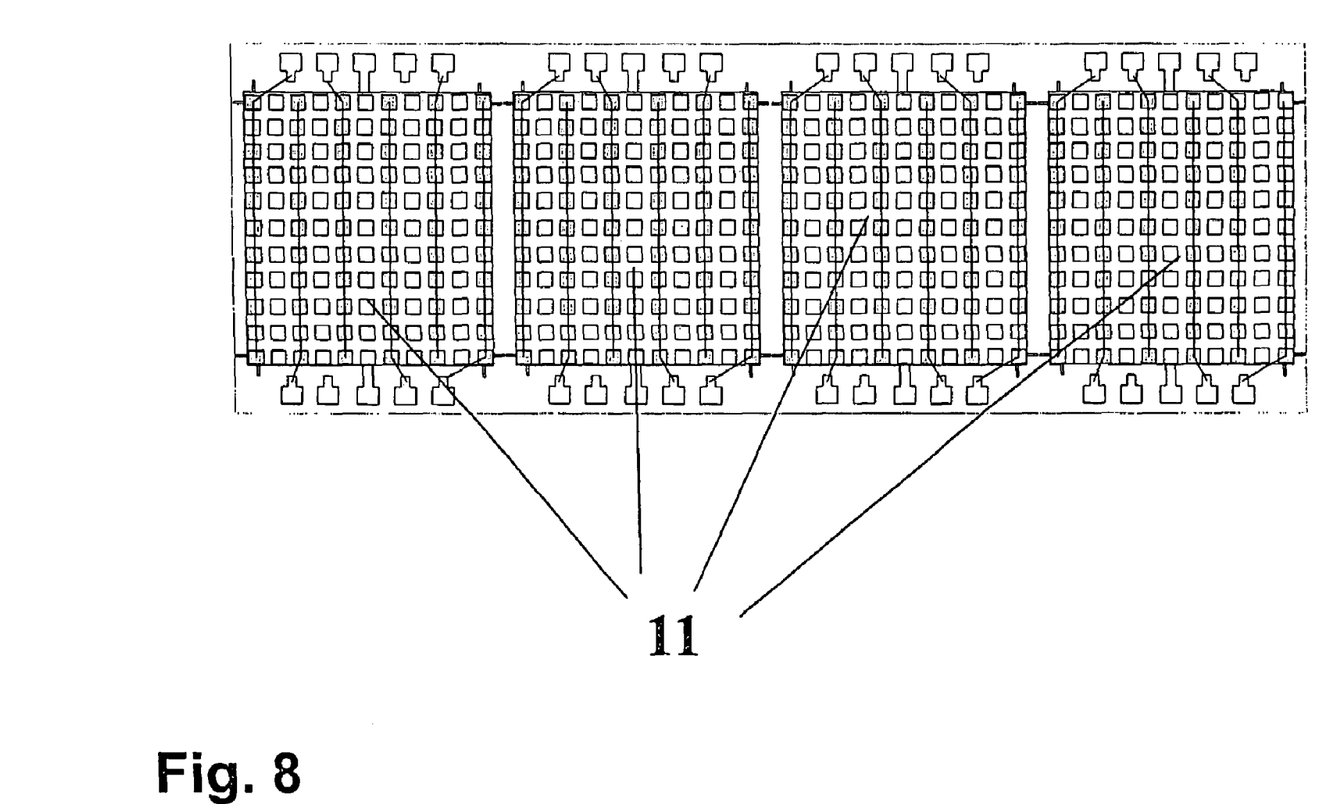

A top view of two strip-like structured transducer arrays 11 is shown in FIG. 5 disposed on a common wafer 7. FIGS. 6 to 8 in contrast show column-like structured transducer arrays disposed on a wafer 7. Herein, in each case a certain number of individual elements are interconnected so as to form individual element groups. By stringing several transducer arrays together on a common conductor plate, ultrasound transducer structures of larger lateral expansion or curved transducer structures can be formed which, provided with a suitable electronic control may form an ultrasound phase array (FIGS. 7 and 8). Since the chances, that the piezoelectric body exceeding a predetermined thickness, fractures increase with an increasing lateral extension of the body, several piezoelectric bodies (or transducer arrays may be arranged side-by-side on a common plate and the bodies are electronically interconnected to form a single ultrasound transducer. In this way, the chances of breakage during the application of the bodies can be reduced and the need for spacers arranged in the covered area can be reduced.

By the electrical interconnection of several columns, in principle, practically any desired active transducer group arrangement (or sensor form) can be generated within the framework of the structure provided by the columns. FIGS. 6 and 7 each show a checkerboard-like arrangement of groups of columns with each body (transmitter array) extending over a 5×5 mm area, wherein nine columns are interconnected to a group of columns. By stringing together several transducer arrays any size of sensor fields can be established (FIG. 7). With a phase-shifted control of the individual column groups, the sound emission of an ultrasound impulse (sound lobe) transmitted can be influenced.

FIG. 8 shows an ultrasound transducer which corresponds to the embodiment shown in FIG. 7 except for an interconnection of column groups in the form of strips. By the structuring and the interconnection of the individual columns, the sensor properties are clearly improved over the strip-like interconnection.

The groups of columns are contacted on the upper electrode by wire connections (electrical connections 6). However, the wire connections must not—or not noticeably—influence the acoustical properties. Contacts formed by soldering or conductive cementing are not possible because of the small lateral extension of the columns or because of the thermal stress on the piezo electric material. Newer techniques prefer the use of conductive foils which provide a contact by cementing under pressure.

In the exemplary embodiment, contacts are established in the upper electrodes on the columns by an ultrasound wire bonding method. The thermal influences are locally limited and very small since the wire thicknesses are relatively small with 30 µm to 70 µm in relation to the electrode surface areas of for example about 300 µm×300 µm. The bonding process can be performed cold so that the piezo-ceramics are not thermally stressed. Contacts are established from the piezo-columns directly to the conductors (bonding areas) or, as shown in FIGS. 6 to 8 from column to column with only one connection to the conductor. The connection to the following electronics is provided for via suitable substantially thicker electrical conductors extending from the conductor (solder areas).

The manufacture of an ultrasound transducer comprises the following individual method steps:

In the manufacture of this embodiment, a piezoelectric body 1 is cemented by a rapidly hardening cement of low viscosity (instant cement on cyanacrylate basis) onto a wafer 7, wherein the spacers 9 and the ground contacts 12 determine the thickness of the cementing gap 10 (see FIGS. 2-4). It is important that the cement hardens without bubbles in order to establish a good acoustic coupling between the wafer 7 and the piezoelectric body 1. To this end, a drop of the cement mentioned above is applied to the center of the covered area 15 (engagement surface) and, upon placement of the piezo electric body onto the drop, is distributed uniformly to the side without forming any bubbles. The spacers 9 must not inhibit this displacement process, that is, they must be so shaped that this outward flow is not interrupted and no air chambers can be formed. The spacers as shown in FIGS. 3 and 4 are disposed at the outer edges or at such locations which are acoustically inactive or have only very little activity or by which the sound waves can easily pass. Since the thickness of the cementing gap 10 is, in the present example with 30 µm, substantially smaller than the wavelength of the acoustic ultrasound signals, at 3 MHz, the acoustic influence of the cement layer on the transducer properties is negligible.

When the piezoelectric body or transducer is pressed onto the spacers 9 and the ground contacts 12, an electrically conductive connection is established between the lower electrode of the piezoelectric body or transducer and the ground contacts 22. The electrically conductive connection can be examined particularly advantageously during the whole manufacturing process by a contact resistance measurement between two ground contacts which are electrically short-circuited via the lower electrode. A smaller resistance value indicates a good contact, which is easily controllable during the manufacturing process. The advantage of this method resides in the fact that the force needed can be relatively small which reduces the chances of breaking the piezoelectric body. A smaller force also has the effect that, upon removing the load on the connection after hardening of the cement, the remaining internal stress level is smaller. This also reduces the chances of a fracture of the cement joint for example during temperature change stress loads or during subsequent mechanical finishing steps which also could lead to a loss of contact and consequently failure of the ultrasound transducer. These disadvantages and limitations are avoided by the described method steps in connection with the use of the spacers and ground contacts. In addition, a high reproduceability of the ultrasound transducers with respect to their acoustic and electrical properties can be achieved.

In addition, wire connections with the dimensions mentioned above to the lower electrode instead of the ground contacts mentioned above in connection with ultrasound transducers particularly with lateral dimensions below about 2 mm and thicknesses below 0.4 mm would establish additional oscillation modes which additionally influence a use as ultrasound transducer.

The compression procedure is completed with the hardening of the cement. A structuring of the piezoelectric body occurs after hardening, wherein a high-quality and reliable, but still relatively inexpensive, structuring of the piezoelectric body can be performed in an advantageous way with the wafer serving as a stable carrier fixed in the structuring device as described above.

Piezo-elements are preferably structured with a wire saw (wafer saw) wherein the cutting depth does not extend over the full thickness of the piezoelectric body, but preferably only so far that a thickness of less than $\lambda/8$ remains and the lower electrode surface remains unstructured. The influence of this unstructured residual thickness area is essentially negligible for the impulse-echo process.

Subsequently, the upper electrode is provided with contacts as described earlier. Then the completed ultrasound transducer, including the electronics, are cast into a housing. In this way, the acoustic attenuation 3 of the ultrasound sensor is adjusted, the bond wires 13 are protected from mechanical stresses and the whole system is made insensitive to outer influences.

All method steps described can be performed automatically using apparatus of the modern SMT and thick film technology for the reliable and inexpensive manufacture of the ultrasound transducers. The ultrasound transducers manufactured in this way are particularly easily reproducible as far as their electrical and acoustic properties are concerned which is important especially for systems which include a large number of sensors or transducers.

The process can be fully automated. Furthermore, at the same time, the required electrical components such as preamplifier and emitter stages can be integrated into, or mounted onto, the wafer. Because of the short distance of the ultrasound transducer from the electronic control devices, electrical disturbances are very small. The quality of the ultrasound signals is therefore substantially improved. With this simple integration of the ultrasound transducers and the electronic equipment, the systems can become much smaller and expenses are reduced.

Literature

[1] EP 1145772 A2
[2] DE 100 50 232 A1
[3] R. Stotzka, H. Widmann, T. Müller, and K. Schlote-Holubek: Prototype of a new 3D ultrasound computer tomography system: transducer design and data recording; presentation on 18 Feb. 2004 in SPIE's Internl. Symposium Medical Imaging 2004 (14-19Feb. 2004 in San Diego, USA)

What is claimed is:

1. An ultrasound transducer comprising:
   a) at least one piezoelectric body (1, 11) with at least a lower and an upper electrode (5),
   b) a coupling layer comprising at least one wafer (7) on which the ultrasound transducer is connected to the lower electrode,
   c) conductor structures (9, 12) of uniform conductor height disposed on the wafer below the piezoelectric bodies which are in contact with the lower electrode and disposed in spaced relationship from the wafer surface, and
   d) the space (10) between the wafer and the piezo electric body at opposite sides of the conductor structure being completely filled with a binding material.

2. An ultrasound transducer as defined in claim 1, wherein the conductor structure extends only under areas of the piezoelectric body which are acoustically inactive or have little activity.

3. An ultrasound transducer as defined in claim 2, wherein the areas are formed by the edge areas of the piezoelectric body.

4. An ultrasound transducer as defined in claim 1, wherein the wafer has an acoustic impedance which is between that of the piezoelectric body and that of water.

5. An ultrasound transducer as defined in claim 1, wherein the binding material is a cement.

6. An ultrasound transducer as defined in claim 5, wherein the cement includes mixed into it particles of a filler material which influences the acoustic impedance and the attenuation behavior of the cement.

7. An ultrasound transducer as defined in claim 1, wherein the piezoelectric bodies are structured by cavities which extend from the upper electrode but not down to the lower electrode.

8. An ultrasound transducer as defined in claim 7, wherein the cavities extend down from the upper electrode at least 80% of the distance to the lower electrode.

9. An ultrasound transducer as defined in claim 7, wherein the cavities are saw cuts defining thereby columns or strip structures.

* * * * *